United States Patent [19]
Josephberg

[11] Patent Number: 6,059,792
[45] Date of Patent: *May 9, 2000

[54] SUTURELESS PARS PLANA VITRECTOMY TOOL

[76] Inventor: Robert Gary Josephberg, 11 Tanglewood Cir., Briarcliff Manor, N.Y. 10510

[*] Notice: This patent is subject to a terminal disclaimer.

[21] Appl. No.: 09/102,990

[22] Filed: Jun. 22, 1998

Related U.S. Application Data

[63] Continuation of application No. 08/632,551, Apr. 15, 1996, Pat. No. 5,989,262.
[51] Int. Cl.⁷ ....................................................... A61F 9/00
[52] U.S. Cl. ............................ 606/107; 604/22; 606/167; 606/171
[58] Field of Search ..................................... 606/107, 159, 606/167, 170, 171, 174, 184, 185, 169, 177; 604/19, 22; 600/562–568

[56] References Cited

U.S. PATENT DOCUMENTS 5,098,438   3/1992   Siepser ..................................... 606/107

Primary Examiner—Glenn K. Dawson
Attorney, Agent, or Firm—Brown, Winick, Graves, Gross, Baskerville & Schoenebaum, P.L.C.; Brett J. Trout

[57] ABSTRACT

An intraocular surgical tool for removing material from an eye of a patient. The tool is provided with a cutting assembly and an aspiration apparatus to remove a portion of vitreous from the eye for inspection and testing. The tool is also fitted with a mechanism for replacing the removed vitreous with saline or similar fluid. The tool is capable of varying cutting speed over a range of fifty cycles per minute. The tool is portable having a housing and battery pack releasably coupled to one another. The cutting assembly is releasably secured to the housing. Accordingly, the housing may be removed and the cutting assembly discarded so that the housing may be sterilized before performing a vitrectomy.

15 Claims, 3 Drawing Sheets

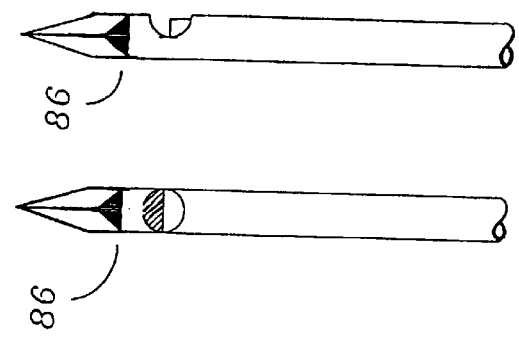
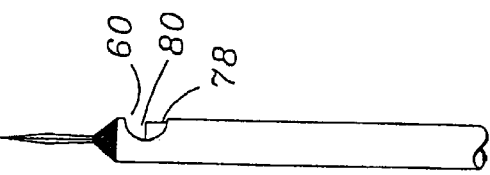
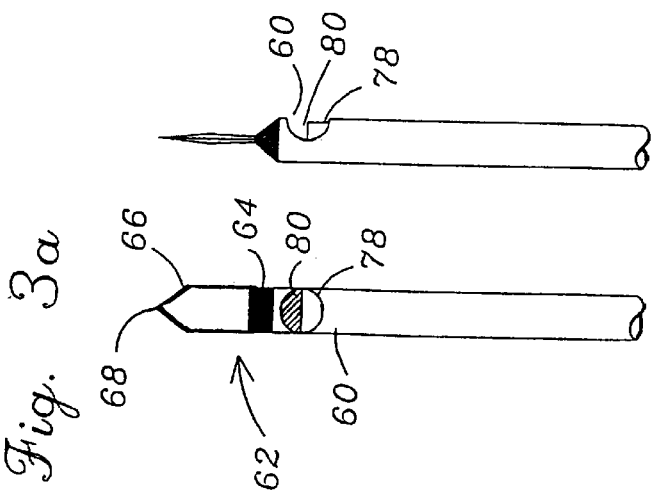

SUTURELESS PARS PLANA VITRECTOMY TOOL

This is a continuation of application Ser. No. 08/632,551 filed on Apr. 15, 1996, now U.S. Pat. No. 5,989,262.

BACKGROUND OF THE INVENTION

Field of the Invention

The present invention relates to a vitrectomy tool and, more particularly, to a sutureless vitrectomy cutter having a cutting assembly small enough to allow the eye to heal without sutures.

Vitreous inflammatory diseases are often associated with a poor prognosis for the patient. Accurate diagnosis and early treatment of endophthalmitis and other acute forms of vitritis is essential. Traditionally, two options have been available for managing a patient with endophthalmitis. The first option is a vitreous tap which may be performed in a doctor's office or operating room. The second option is a pars plana vitrectomy which, due to the required equipment and complexity of the operation, is performed in an operating room.

While vitreous taps may be safely performed in an office setting, as well as in the operating room, many times it is difficult to aspirate liquid vitreous. This is due to the density of the vitreous cavity and the gauge of the needle (eighteen to twenty gauge) required to aspirate the vitreous. The vitreous tap has the advantage of rapid diagnosis and treatment. The major disadvantages of the vitreous tap include, but are not limited to, vitreous traction, retinal tears and/or retinal detachments.

Pars plana vitrectomy can overcome some of the problems associated with vitreous tap. Pars plana vitrectomy provides a larger vitreous sample for analysis, which may increase the diagnostic yield of organisms. It also may facilitate intraocular antibiotic penetration and allow better clearance of the toxins. The major disadvantage of the pars plana vitrectomy is that it is traditionally performed in an operating room. Operating room scheduling, rooms set-up, equipment set-up and patient admitting and testing may cause delays. Since time is of the essence with endophthalmitis, any delays in diagnosis and treatment can have devastating effects. Additionally, pars plana vitrectomy is a more difficult procedure involving several steps, and is associated with the possibility of more complications, than the vitreous tap.

After a pars plana vitrectomy is performed, it is often necessary to suture closed the opening made in the eye to perform the vitrectomy. Suturing typically involves additional problems such as increased time in the operating room and increased cost for the sutures. Sutures also increase the possibility of infection in and along the suture tract. To overcome the problems associated with suturing an eye after a vitrectomy, it is known in the art to use a vitrectomy instrument with a cutting assembly small enough to be used through an incision small enough so as not to require sutures.

These prior art sutureless pars plans vitrectomy instruments are very large, typically weighing fifty pounds or more with their transport carriage occupying five cubic feet or more of operating room space.

The size of these instruments is typically governed by the power source required to run and the need for stability during the vitrectomy procedure itself. Due to the size of these instruments, however, moving them out of the way, transporting them from room to room, or transporting them in a vehicle is cumbersome. It would therefore be desirable to provide a smaller, portable vitrectomy instrument which could be used in a doctor's office and which could be easily transported and stored.

Although the above-described techniques are adapted to provide a vitreous sample for testing, as noted above, both the vitreous tap and the pars plana vitrectomy have drawbacks for the patient. Neither technique combines the ease of the vitreous tap with the safety of the pars plana vitrectomy in a portable apparatus. The difficulties encountered hereinabove are sought to be eliminated by the present invention.

SUMMARY OF THE INVENTION

The present invention comprises a sutureless intraocular surgical tool for removing material from an eye of a patient. The tool is provided with a housing having a proximal end and a distal end. A cutter assembly is secured to the proximal end of the housing. The cutter assembly includes an outer cutter which has a sidewall defining a longitudinal bore, the longitudinal bore being provided with an aperture. The outer cutter is of a size sufficient to fit through an opening in the eye small enough to heal without sutures. The tool also includes an inner cutter, which has a cutting edge and which is telescopically received in the longitudinal bore of the outer cutter. The inner cutter is adapted for travel across a cutting edge of the aperture. A linear actuator is provided in the housing and drivably coupled to the inner cutter. The tool is also provided with means releasably coupled to the linear actuator for powering the linear actuator, and means for varying a cycling speed of said linear actuator over a range of at least fifty cycles per minute.

In the preferred embodiment of the present invention the outer cutter is of a size sufficient to fit through an opening in the eye small enough to heal without sutures. The cutter assembly is releasably secured to the housing and may be disposable or nondisposable. The tool is provided with a solenoid actuator or similar varying means to vary the cycling speed of the linear actuator. The tool may be provided with means in operable communication with the longitudinal bore for providing suction to the longitudinal bore.

The method of the present invention involves manually placing the outer cutter into the eye transconjunctivally, through the pars plana. A sample of vitreous is cut from the eye and aspirated through the longitudinal bore to a sample container. The outer cutter is then manually removed from the eye. Preferably, the method involves allowing the eye to heal without suture.

BRIEF DESCRIPTION OF THE DRAWINGS

FIG. 3a is an enlarged bottom plan view of the blade, inner cutter and outer cutter of the guillotine cutter of FIG. 1;

FIG. 3b is an enlarged side elevation of the blade, inner cutter and outer cutter of FIG. 3a;

FIG. 4a is an enlarged bottom plan view of an alternative stiletto tip which may be used with the guillotine cutter of FIG. 1;

FIG. 4b is an enlarged side elevation of the alternative stiletto tip of FIG. 4a;

FIG. 5a is an enlarged bottom plan view of an alternative broadhead tip which may be used with the guillotine cutter of FIG. 1;

FIG. 5b is an enlarged side elevation of the alternative broadhead tip of FIG. 5a; and FIG. 5c is an enlarged top elevation of the alternative broadhead tip of FIG. 5a.

DETAILED DESCRIPTION OF THE PREFERRED EMBODIMENT

Figure 1:
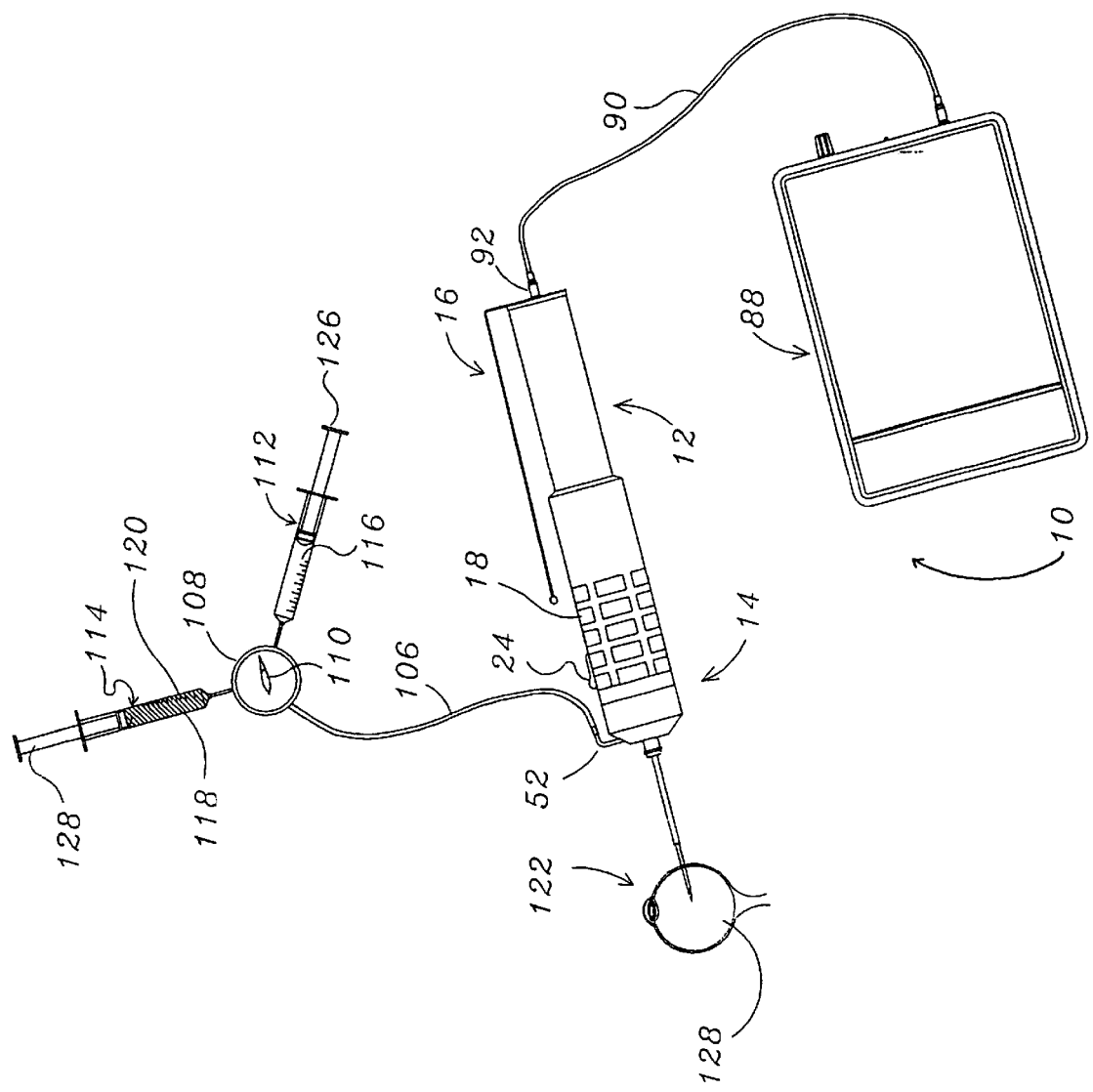
FIG. 1 is a side elevation of the guillotine cutter of the present invention shown with the cutting assembly positioned within an eye.
Figure 2:
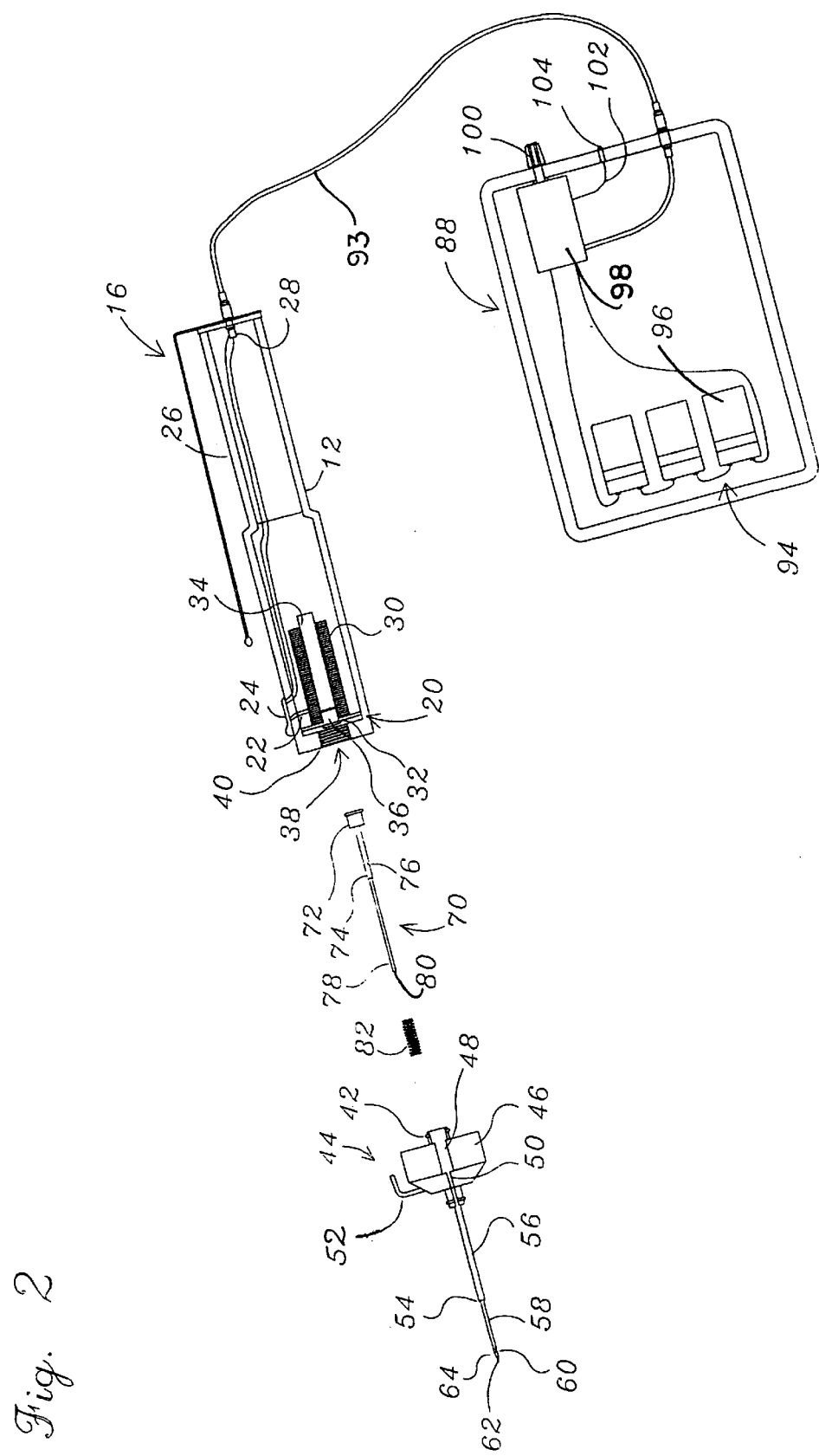
FIG. 2 is a partial exploded side elevation in cross-section showing the guillotine cutter of FIG. 1.

With reference to the drawings, shown in FIG. 1 is a guillotine cutter 10 having a housing 12 with a proximal end 14 and a distal end 16. Preferably three inches long, one-half inches in diameter, and weighing less than one pound, the housing 12 is sized to fit within the hand of a user (not shown). The housing 12 is provided with a plurality of studs 18 as shown in FIG. 1 or a similar non-stick surface to prevent slippage of the guillotine cutter 10 from the hand of a user (not shown). As shown in FIG. 2, positioned within the housing 12 is a linear actuator, which, in the preferred embodiment is a solenoid 20. The solenoid 20 is operably coupled by wires 22 to a switch 24 slidably received on the housing 12. The switch 24, in turn, is coupled via a set of wires 26 to a plug jack 28 provided on the distal end 16 of the housing 12.

The solenoid 20 includes an outer wire coil 30 defining a bore 32 in which slides an iron core 34. Secured to one end of the iron core 34 is a solenoid pusher 36 which may be constructed of tin, a steel manganese nickel alloy or a similar non-magnetic material. The solenoid 20 is secured within the housing 12 in such a manner that the solenoid pusher 36 may reciprocate into and out of a bore 38 provided in the proximal end 14 of the housing 12. As shown in FIG. 2, the bore 38 is provided with threads 40 for mating engagement with threads 42 provided on an outer cutter assembly 44. The outer cutter assembly 44 includes an anodized aluminum cap 46 provided with a throughbore 48. The throughbore 48 narrows to a smaller shaft 50 which is in communication with a fluid port 52 secured to the exterior of the cutter assembly 44. Extending from the end of the cap 46 is the outer cutter 54. The outer cutter 54 is constructed of twenty gauge stainless steel tubing 56 which narrows to twenty-three gauge stainless steel tubing 58 approximately eighteen millimeters from the end of the cap 46. The twenty-three gauge stainless steel tubing 58 extends an additional twelve millimeters beyond the end of the twenty gauge stainless steel tubing 56. Near the end of the twenty-three gauge stainless steel tubing 58 is an aperture 60 one-half of one millimeter in diameter. The edges of this aperture 60 are beveled or sharpened to provide a cutting edge along the edge of the aperture 60. Connected to the end of the twenty-three gauge stainless steel tubing 58 is a surgical blade 62 secured to the twenty-three gauge stainless steel tubing by silver solder 64 or a similar securement method. As shown in FIGS. 3a and 3b, the surgical blade 62 is generally flat with a beveled cutting edge 66 which tapers to a point 68 and which may be diamond coated.

As shown in FIG. 2, the cutter 10 is also provided with an inner cutter 70 having a cutter pusher 72 secured to a length of twenty-three gauge stainless steel tubing 74 extending twelve millimeters beyond the cutter pusher 72. The twenty-three gauge stainless steel tubing 74 is provided with an aperture 76 one and one-tenth millimeters in diameter. The twenty-three gauge stainless steel tubing 74 is secured to a length of twenty-seven gauge stainless steel tubing 78 extending thirty-three millimeters beyond the end of the twenty-three gauge stainless steel tubing 74. The end of the twenty-seven gauge stainless steel tubing 78 is provided with a sharpened cutting edge 80. Provided around the inner cutter 70 is a return spring 82 which fits within the through-bore 48. As shown in FIGS. 2, 3a and 3b, when the inner cutter 70 is placed within the outer cutter assembly 44, the sharpened cutting edge 80 of the inner cutter 70 is capable of movement back and forth across the aperture 60 of the twenty-three gauge stainless steel tubing 58.

Alternatively, instead of the surgical blade 62 as shown in FIGS. 3a and 3b, the cutter may be provided with a stiletto tip 84 as shown in FIGS. 4a and 4b or a broad-head tip 86 as shown in FIGS. 5a, 5b and 5c.

The twenty-three gauge stainless steel tubing 58 is designed small enough so that no sutures are required to repair an incision made by the surgical blade 62 secured to the twenty-three gauge stainless steel tubing 58 (FIG. 2). The dimensions of the inner cutter 70 are dictated by the dimensions of the outer cutter assembly 44. The inner cutter 70 is provided with dimensions designed to move close enough against the outer cutter 54 to shear material protruding through the cutting aperture 60 into the outer cutter 54. The inner cutter 70 is also small enough so as to not to generate undue friction as it moves across the interior of the outer cutter 54.

As shown in FIGS. 1 and 2, a power supply pack 88 is coupled to the distal end 16 of the housing 12 via a power transfer cable 90. The power transfer cable 90 is provided on one end with a plug 92 for releasable coupling into the plug jack 28 provided in the distal end 16 of the housing 12. The power supply pack 88 is sized to be hand held, preferably three and one-half inches wide, five and one-half inches long, one and one-half inches deep and weighing less than two pounds. Of course, while the guillotine cutter 10 of the present invention may be of any desired dimensions and weight, the guillotine cutter 10, including the housing 12 and power supply pack 88, is preferably less than twenty cubic inches and weighs less than ten pounds. While the power supply pack 88 is sized to be hand held, the power supply pack 88 may be rested on a table during performance of a vitrectomy. The hand held size and light weight of the present invention allows the guillotine cutter 10 to be more easily manipulated, transported and stored. The small size also aids in sterilization and decreases preparation time.

As shown in FIG. 2, the power supply pack 88 is provided with a power source 94 which, in the preferred embodiment, is three nine-volt batteries 96. Also provided within the power supply pack 88 is a variable speed solenoid actuator 98 such as any type well known in the art. The solenoid actuator 98 is provided with an adjustment knob 100 mounted on the exterior of the power supply pack 88. Coupled to the solenoid actuator 98 by a set of wires 102 is a light emitting diode 104 which serves as a battery power indicator.

Coupled to the fluid port 52 is a transfer tube 106 as shown in FIG. 1. The transfer tube 106 is connected to a three-way stopcock 108. The three-way stopcock 108 is provided with a valve 110 which determines what material flows through the transfer tube 106 and in what direction. Secured to the three-way stopcock 108 is an aspiration syringe 112 and an irrigation syringe 114. The aspiration syringe 112 is provided with a sample chamber 116, while the irrigation syringe 114 is provided with a fluid chamber 118. In the preferred embodiment the fluid chamber 118 is provided with saline 120, but may, of course be provided with air or a similar fluid.

To use the guillotine cutter 10 of the present invention, a patient (not shown) is placed in a supine or sitting position and an eye 122 of the patient is prepared for surgery (FIG. 1) . Anesthetic may be administered retrobulbar, peribulbar or subconjunctival. Preferably, a portable microscope, or slit lamp and indirect ophthalmoscopy (not shown) is used to view the operation. A lid speculum (not shown) such as those well-known in the art is inserted into the eye 122. The guillotine cutter 10 is then used to place an incision 124 transconjunctivally through the pars plana approximately 3.5 millimeters posterior to the limbus or through the anterior segment (FIG. 1). The switch 24 is used to actuate the cutter 10 (FIGS. 1 and 2). Once the switch 24 has been actuated, the solenoid actuator 98 alternately draws the iron core 34 into the bore 32 and releases the iron core 34. As the iron core 34 is drawn into the bore 32, the solenoid pusher 36 is moved out of the bore 32 into the cutter pusher 72. As the cutter pusher 72 is driven by the solenoid 20, the cutting edge 80 of the inner cutter 70 moves across the aperture 60 provided in the twenty-three gauge stainless steel tubing 58. As the solenoid actuator 98 releases the iron core 34, the spring 82 drives the cutter pusher 72 toward the solenoid 20. The cutter pusher 72, in turn, forces the solenoid pusher 36 into the iron core 34 and the iron core 34 partially out of the bore 32. The solenoid actuator 98 may be adjusted with the adjustment knob 100 to cycle the inner cutter 70 at the appropriate speed. In the preferred embodiment the solenoid actuator 98 is capable of adjusting the cutting speed of the guillotine cutter 10 from between sixty to three hundred cycles per minute. The adjustment knob 100 of the solenoid actuator 98 is typically adjusted to achieve a cutter speed of about one hundred cycles per minute. The three-way stopcock 110 is positioned as shown in FIG. 1 and a plunger 126 of the aspiration syringe 112 is pulled back to draw vitreous 128 into the cutting aperture 60 (FIGS. 1 and 3a). As the cutting edge 80 of the inner cutter 70 moves across the cutting aperture 60, a portion of vitreous 128 is sliced off. As the plunger 126 of the aspiration syringe 112 is pulled back, the severed portion of vitreous 128 is drawn through the inner cutter 70 and out of the aperture 76. The vitreous 128 is drawn through the fluid port 52 and transfer tube 106 into the sample chamber 116 of the aspiration syringe 112. This continues until an appropriate amount of vitreous 128 has been drawn into the sample chamber 116.

Once the appropriate amount of vitreous 128 has been collected, the three-way stopcock 108 adjusted to allow the saline 120 to be injected from the irrigation syringe 114, through the transfer tube 106 and into the eye 122. As a plunger 128 of the irrigation syringe 114 is depressed the saline 120 flows through the three-way stopcock 108 through the transfer tube 106 and through the fluid port 52. The saline 120 moves through the aperture 76 of the inner cutter 70 and through the inner cutter 70. The saline 120 moves out of the inner cutter 70 and through the cutting aperture 60 into the eye 122. Once an appropriate amount of saline 120 has been injected into the eye 122, the guillotine cutter 10 is removed from the eye 122.

The guillotine cutter 10 is preferably removed from the eye 122 with the cutting edge 80 of the inner cutter 70 not covering the cutting aperture 60 so as to prevent torsional damage to the vitreous 128 from being caught between the cutting edge 80 of the inner cutter 70 and the cutting aperture 60. Due to the small gauge of the twenty-three gauge stainless steel tubing 58, the incision 124 is small enough that no sutures are required for the eye 122 to heal.

After the operation, distilled water (not shown) or a similar cleansing agent is forced through the transfer tube 106 and out the cutting aperture 60. The cleansing agent is then forced through the cutting aperture 60 and out the transfer tube 106 to clear the guillotine cutter 10 of any remaining vitreous 128 or other debris. Once the guillotine cutter 10 has been cleansed, the plug 92 and a power cord 93 attached thereto are removed from the plug jack 28. The outer cutter assembly 44 is unscrewed from the housing 12 and the power cord 93, outer cutter assembly 44, inner cutter 70, fluid transfer tube 106, spring 82 and housing may be sterilized by ethylene oxide or steam autoclave according to recognized standards and recommended practices. Preferably, however, only the housing 12 and power cord 93 are sterilized, while the outer cutter assembly 44, inner cutter 70, fluid transfer tube 106 and spring 82 are discarded. A new, sterilized outer cutter assembly 44, inner cutter 70, fluid transfer tube 106 and spring 82 are then assembled on the housing 12 as described above and the guillotine cutter 10 is thereafter again ready for use.

Although the invention has been described with respect to a preferred embodiment thereof, it is to be understood that it is not to be so limited, since changes and modifications can be made therein which are within the full intended scope of this invention as defined by the appended claims. For example, it is anticipated that various styles of tips may be secured to the stainless steel twenty-three gauge tubing 58 to make various types of incisions in the eye 122 of a patient. Additionally, it is anticipated that various types and dimensions of blades and cutters may be used to perform the sutureless vitrectomy described above. It is also anticipated that the cutter may be mechanically, electrically or pneumatically actuated.

What is claimed is:

1. A sutureless intraocular surgical tool for removing material from an eye of a patient comprising:
   (a) a housing having a proximal end and a distal end;
   (b) an outer cutter coupled to said proximal end of said housing, wherein said outer cutter is of a size sufficient to fit through an opening in the eye small enough to heal without sutures, said outer cutter having a sidewall defining a longitudinal bore, said sidewall being provided with an aperture;
   (c) an inner cutter having a cutting edge telescopically received in said longitudinal bore of said outer cutter and adapted for travel of said cutting edge across said aperture;
   (d) a linear actuator provided within said housing and driveably coupled to said inner cutter;
   (e) means releasably coupled to said linear actuator for powering said linear actuator; and
   (f) further comprising means coupled to said powering means for varying a cycling speed of said linear actuator wherein said varying means is a solenoid actuator, coupled to said linear actuator, and capable of varying cycling of said linear actuator over a range of at least forty cycles per minute.

2. The intraocular surgical tool of claim 1, wherein said housing is hand held.

3. The intraocular surgical tool of claim 1, wherein said outer cutter is no larger than twenty-three gauge.

4. The intraocular surgical tool of claim 1, wherein said powering means is a battery pack.

5. The intraocular surgical tool of claim 1, wherein said outer cutter tapers from no greater than twenty (20) gauge to no greater than twenty-three (23) gauge.

6. The intraocular surgical tool of claim 1, wherein said housing, said outer cutter, said inner cutter, said linear actuator and said powering means collectively weigh no greater than ten (10) pounds.

7. The intraocular surgical tool of claim 1, further comprising means operably coupled to said housing for stopping and starting said linear actuator.

8. The intraocular surgical tool of claim 1, wherein said housing is substantially impervious to sterilization by ethylene oxide.

9. The intraocular surgical tool of claim 1, wherein said housing is substantially impervious to steam autoclave sterilization.

10. The intraocular surgical tool of claim 1, wherein said outer cutter and said inner cutter are disposable.

11. The intraocular surgical tool of claim 1, further comprising suctioning means in operable communication with said longitudinal bore for applying a suction to said longitudinal bore.

12. The intraocular surgical tool of claim 11, wherein said suctioning means is a suction tube provided in operable communication with said longitudinal bore.

13. The intraocular surgical tool of claim 12, further comprising means for injecting fluid into said longitudinal bore.

14. The intraocular surgical tool of claim 13, wherein said injecting means is an injection tube in operable communication with said suction tube.

15. The intraocular surgical tool of claim 14, further comprising a three-way stopcock in operable communication with said longitudinal bore, said suction tube, and said injecting means.

* * * * *